United States Patent [19]

Vinick

[11] 4,321,391

[45] Mar. 23, 1982

[54] PREPARATION OF L-ASPARTIC ACID N-THIOCARBOXYANHYDRIDE

[75] Inventor: Fredric J. Vinick, Waterford, Conn.

[73] Assignee: Pfizer, Inc., New York, N.Y.

[21] Appl. No.: 204,135

[22] Filed: Nov. 5, 1980

[51] Int. Cl.$^3$ ............................................ C07D 277/04
[52] U.S. Cl. .................................................... 548/183
[58] Field of Search ........................................ 548/183

[56] References Cited

U.S. PATENT DOCUMENTS 3,846,398 11/1974 Hirschmann et al. ........... 260/112.5
4,256,897 3/1981 Vinick ................................. 548/183

OTHER PUBLICATIONS

J. Org. Chem., vol. 36, pp. 49 to 59 (1971); Dewey et al.
Bull. Chem. Soc. Japan, vol. 45, pp. 2208 to 2209 (1972); Ariyoshi et al.
Bull. Chem. Soc. Japan, vol. 46, pp. 1893 to 1895 (1973); Ariyoshi et al.

Primary Examiner—Natalie Trousof
Assistant Examiner—Frederick W. Pepper
Attorney, Agent, or Firm—Charles J. Knuth; Peter C. Richardson

[57] ABSTRACT

L-Aspartic acid N-thiocarboxyanhydride is prepared by the reaction of an L-aspartic anhydride addition salt with carbonyl sulfide.

13 Claims, No Drawings

PREPARATION OF L-ASPARTIC ACID N-THIOCARBOXYANHYDRIDE

BACKGROUND OF THE INVENTION

This invention relates to the preparation of L-aspartic acid N-thiocarboxyanhydride, which is a useful intermediate for the synthesis of peptides. In particular, L-aspartic acid N-thiocarboxyanhydride is useful for reaction with L-phenylalanine lower alkyl esters to form L-aspartyl-L-phenylalanine lower alkyl esters, which are useful as potent sweetening agents for use in foodstuffs and beverages. The methyl ester is especially preferred as a sweetening agent.

The preparation of amino acid N-thiocarboxyanhydride derivatives is described in J. Org. Chem. 36, 49 (1971). One method described therein is the reaction of an amino acid with carbonyl sulfide in an alkali metal hydroxide solution, to form an alkali metal salt of the amino acid thiocarbamate, which is then reacted with a phosphorus trihalide to provide a mixture of the N-thiocarboxyanhydride and the N-carboxyanhydride. However, in efforts to apply this method to the preparation of L-aspartic acid N-thiocarboxyanhydride, only low yields of product have been obtained.

SUMMARY OF THE INVENTION

It has now been found that L-aspartic acid N-thiocarboxyanhydride may be prepared in improved yield by the direction reaction of an L-aspartic anhydride addition salt with carbonyl sulfide in a non-protic reaction medium in the present of a non-nucleophilic base at a temperature from about $-78°$ C. to about $25°$ C. The reaction is preferably conducted in an alkyl acetate solvent, especially ethyl acetate, in the presence of a tertiary amine base, especially triethylamine, preferably at a temperature from about $-78°$ C. to $0°$ C.

DETAILED DESCRIPTION OF THE INVENTION

L-Aspartic acid N-thiocarboxyanhydride is prepared in accord with the present process by the reaction of an L-aspartic anhydride addition salt with carbonyl sulfide. Under the conditions described hereinafter, optimum yields of L-aspartic acid N-thiocarboxyanhydride may be obtained and undesired side reactions, especially polymerization of aspartic anhydride and the formation of polypeptides, are maintained at a minimum. Suitable addition salts of L-aspartic anhydride for use in the present process are those with mineral or organic acids, including the hydrohalides, sulfates, alkyl sulfates, mesylate, tosylate, formate, benzoate and the like. The hydrohalide salts, especially the hydrochloride and hydrobromide, are preferred starting materials for the present process. The addition salts of L-aspartic anhydride are known compounds and may be prepared by methods described, for example, in Bull. Chem. Soc. Japan 45, 2208 (1972) and Bull. Chem. Soc. Japan 46, 2611 (1973). It will be understood that L-aspartic anhydride is unstable as the free base and that the addition salts thereof provide a suitable stable starting material for use in the present process. However, without wishing to be bound by any particular theory of the mechanism of the reactions of the present process, it is believed that the free base will be formed in situ and is the species that participates in the reaction with carbonyl sulfide. Accordingly, the particular addition salt employed as a starting material is not critical to the present process and any salt or other derivative which would provide the L-aspartic anhydride free base in situ in the reaction medium can be employed and such compounds are intended to be embraced by the specification and claims hereof.

The reaction of the L-aspartic anhydride addition salt and carbonyl sulfide is generally conducted in a non-protic organic reaction medium, for example an ether such as tetrahydrofuran, dioxane, diethyl ether and the like, or in an alkyl acetate having from 1 to 4 carbon atoms in the alkyl group, especially in ethyl acetate. The L-aspartic acid addition salt is preferably employed at an initial molar concentration of about 0.1 M to 1.0 M, most preferably from about 0.1 M to about 0.25 M.

The reaction is conducted in the presence of a non-nucleophilic base. Suitable bases include tertiary amines and weak inorganic bases such as alkali metal carbonates. Preferred bases are dialkyl pyridines and trialkylamines having from 1 to 3 carbon atoms in each alkyl group, preferably triethylamine. In order to obtain optimum yields of the desired L-aspartic acid N-thiocarboxyanhydride, it is preferred to employ at least two equivalents of base relative to the L-aspartic anhydride addition salt. However, lower amounts of the base may be employed with correspondingly lower yields obtained.

The reaction is generally conducted at a temperature from about $-78°$ C. to about $25°$ C. preferably about $-78°$ C. to $0°$ C., the lower temperatures generally allowing higher yields. The reaction is effected by contacting the L-aspartic anhydride addition salt in the non-protic reaction medium with carbonyl sulfide, for example by bubbling carbonyl sulfide gas into the organic reaction medium, preferably while stirring or otherwise agitating the reaction medium. The time for substantially complete reaction to occur will vary according to the reaction temperature, but will generally be from about 1 to 10 hours.

The desired L-aspartic acid N-thiocarboxyanhydride will be obtained in the reaction medium as a salt. Acidification of the reaction medium, for example by addition of a mineral acid such as hydrochloric or sulfuric acid, will form the L-aspartic acid N-thiocarboxyanhydride as the free acid. The desired product is then readily recovered from the reaction medium by conventional methods, for example by removal of the organic reaction medium, for example by evaporation under reduced pressure, to give the desired solid L-aspartic acid N-thiocarboxyanhydride. Under the preferred conditions of the present process, especially the preferred low initial concentrations of L-aspartic anhydride addition salt, as described above, the concentration of the L-aspartic acid N-thiocarboxyanhydride produced will be relatively low and under these conditions the N-thiocarboxyanhydride is substantially soluble, even in the preferred alkyl acetate reaction medium. At higher concentrations, especially above about 0.75 M, L-aspartic acid N-thiocarboxy anhydride will precipitate directly from solution when formed in alkyl acetate solvents and is thereby readily recovered by filtration of the solid product.

The L-aspartic acid N-thiocarboxyanhydride produced can be used in the formation of peptides, for example in the preparation of L-aspartyl-L-phenylalanine lower alkyl esters, useful as sweetening agents, by reaction with L-phenylalanine lower alkyl esters. The amino acid coupling reaction is generally conducted at a pH from about 8 to 10 preferably about 9 at a temperature in the range about −10° C. to 40° C., preferably 0° C. to 10° C. The intermediate N-thiocarboxy anhydride dipeptide derivative formed is then converted to the desired L-aspartyl-L-phenylalanine lower alkyl ester by adjusting the pH of the reaction solution to about 2 to 6 preferably about 4.5 to 5.5.

The present invention is illustrated by the following examples. However, it will be understood that the invention is not limited to the specific details of these examples.

EXAMPLE 1

L-Aspartic anhydride hydrochloride (3.02 g, 20 mmol) (Bull. Chem. Soc. Japan, 45, 2208 (1972)) was suspended in 150 ml of ethyl acetate at −78° C.; carbonyl sulfide gas was then bubbled into the solution over a period of 10 minutes. Triethylamine (5.6 ml. 40 mmol) was added in one portion at −78° C. Carbonyl sulfide addition was continued for 30 minutes and then the reaction mixture was stirred for 4 hours at −78° C. The cold solution was quenched with 50 ml of 1 N hydrochloric acid and allowed to warm to room temperature. The layers were separated and the aqueous phase extracted with a second portion (100 ml) of ethyl acetate. The clear, colorless organic extracts were dried over anhydrous magnesium sulfide and evaporated in vacuo. The white crystalline residue was digested in ethyl ether, collected by filtration, and dried. The yield of L-aspartic acid N-thiocarboxyanhydride was 1.78 g (51%).

nmr (DMSO-$d_6$)$\delta$ 2.83 (d, 2H, J=5.0 Hz), 4.70 (t, 1H, J=5.0 Hz), 9.23 (bs, 2H, ex).

EXAMPLE 2

L-Aspartic anhydride hydrochloride (6.04 g, 40 mmol) was suspended in 300 ml of ethyl acetate at −78° C.; carbonyl sulfide gas was then bubbled into the solution over a period of 10 minutes. Triethylamine (11.1 ml, 80 mmol) was added in one portion at −78° C. Carbonyl sulfide addition was continued for 30 minutes, and then the reaction mixture was stirred for 1 hour at −78° C. The cold solution was quenched with 100 ml of 1 N hydrochloric acid and worked up as described in Example 1. The isolated yield of L-aspartic acid N-thiocarboxyanhydride was 2.83 g (40%). This material was characterized by optical rotation, tlc, and nmr and found to be identical with an authentic sample of L-aspartic acid N-thiocarboxyanhydride.

EXAMPLE 3

L-Aspartic anhydride hydrochloride (6.04 g, 40 mmol) was suspended in 100 ml of ethyl acetate at −78° C.; carbonyl sulfide gas was then bubbled into the solution over a period of 10 minutes. Triethylamine (11.1 ml, 80 mmol) was added in one portion at −78° C. Carbonyl sulfide addition was continued for 30 minutes, and then the reaction mixture was stirred for 1 hour at −78° C. The cold solution was quenched with 50 ml of 2 N hydrochloric acid and worked up as described in Example 1. The isolated yield of L-aspartic acid N-thiocarboxyanhydride was 2.63 g (38%).

EXAMPLE 4

L-Aspartic anhydride hydrochloride (6.04 g, 40 mmol) was suspended in 100 ml of ethyl acetate at −78° C.; carbonyl sulfide gas was then bubbled into the solution over a period of 10 minutes. Triethylamine (5.6 ml, 40 mmol) was added in one portion at −78° C. Carbonyl sulfide addition was continued fo 30 minutes and then the reaction mixture was stirred for 1 hour at −78° C. The cold solution was quenched with 50 ml of 1 N hydrochloric acid and worked up as described in Example 1. The isolated yield of L-aspartic acid N-thiocarboxyanhydride was 1.62 g (23%).

EXAMPLE 5

L-Aspartic anhydride hydrochloride (6.04 g, 40 mmol) was suspended in 100 ml of ethyl acetate at 0° to 10° C.; carbonyl sulfide gas was then bubbled into the solution over a period of 10 minutes. Triethylamine (5.6 ml, 40 mmol) was added in one portion at 0° to 10° C. Carbonyl sulfide addition was continued for 30 minutes and then the reaction mixture was stirred for 1 hour at 0° to 10° C. The solution was quenched with 50 ml of 1 N hydrochloric acid and worked up as described in Example 1. The isolated yield of L-aspartic acid N-thiocarboxyanhydride was 0.99 g (14%).

EXAMPLE 6

L-Aspartic anhydride hydrochloride (3.02 g, 20 mmol) was suspended in 150 ml of tetrahydrofuran at −78° C.; carbonyl sulfide gas was then bubbled into the solution over a period of 10 minutes. Triethylamine (5.6 ml, 40 mmol) was added in one portion at −78° C. Carbonyl sulfide addition was continued for 30 minutes and then the reaction mixture was stirred for 4 hours at −78° C. The cold solution was quenched with 2.22 ml (40 mmol) of concentrated sulfuric acid and allowed to warm to room temperature. Anhydrous magnesium sulfate was added, the solution was filtered, and the solvent was evaporated in vacuo. The residual gummy solid was digested in water to give granular white crystals. The product was collected by filtration, washed with a small quantity of ethyl ether, and dried in vacuo. The isolated yield of L-aspartic acid N-thiocarboxyanhydride was 1.30 g (37%).

I claim:

1. A process for the preparation of L-aspartic acid N-thiocarboxyanhydride comprising contacting an L-aspartic anhydride addition salt with carbonyl sulfide in a non-protic reaction medium in the presence of a non-nucleophilic base at a temperature from about −78° C. to about 25° C.

2. A process according to claim 1 wherein the temperature is from about −78° C. to 0° C.

3. A process according to claim 1 wherein said reaction medium is an alkyl acetate having from 1 to 4 carbon atoms in the alkyl group.

4. A process according to claim 3 wherein said alkyl acetate is ethyl acetate.

5. A process according to claim 1 wherein said base is a tertiary amine base.

6. A process according to claim 5 wherein said base is a trialkylamine having from 1 to 3 carbon atoms in each alkyl group.

7. A process according to claim 6 wherein said trialkylamine is triethylamine.

8. A process of claim 1 employing about two equivalents of said base.

9. A process according to claim 1 wherein said salt of L-aspartic anhydride is a hydrohalide salt.

10. A process according to claim 9 wherein said salt is the hydrochloride.

11. A process according to claim 9 wherein said salt is employed at an initial concentration of about 0.1 to 1.0 Molar.

12. A process according to claim 11 wherein said initial concentration is from about 0.1 to 0.25 Molar.

13. A process according to claim 1 wherein a 0.1 to 0.25 Molar solution of an L-aspartic anhydride hydrohalide salt in ethyl acetate is contacted with carbonyl sulfide in the presence of about two equivalents of triethylamine at a temperature from about −78° C. to 0° C.

* * * * *